United States Patent
Kulkarni et al.

(10) Patent No.: US 9,224,660 B2
(45) Date of Patent: Dec. 29, 2015

(54) TUNING WAFER INSPECTION RECIPES USING PRECISE DEFECT LOCATIONS

(71) Applicant: KLA-Tencor Corporation, Milpitas, CA (US)

(72) Inventors: Ashok V. Kulkarni, San Jose, CA (US); Lisheng Gao, Saratoga, CA (US); Junqing Huang, Fremont, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 14/470,916

(22) Filed: Aug. 27, 2014

(65) Prior Publication Data

US 2015/0062571 A1 Mar. 5, 2015

Related U.S. Application Data (60) Provisional application No. 61/872,493, filed on Aug. 30, 2013, provisional application No. 61/872,507, filed on Aug. 30, 2013.

(51) Int. Cl.
*G01N 21/00* (2006.01)
*H01L 21/66* (2006.01)
*G01N 21/95* (2006.01)

(52) U.S. Cl.
CPC ............. *H01L 22/12* (2013.01); *H01L 22/20* (2013.01); *G01N 21/9501* (2013.01)

(58) Field of Classification Search
CPC ............ G01N 23/2251; G01N 23/225; G01N 21/9501; G01N 21/95607; G01N 2021/151; G01N 21/94; G01N 23/20; G01N 21/9503; G01N 2021/8864; G01N 2021/9513; G01N 2021/96515; G01N 21/95; G01N 21/956
See application file for complete search history.

(56) References Cited

U.S. PATENT DOCUMENTS

| | | | |
|---|---|---|---|
| 7,485,858 B1 * | 2/2009 | Obara et al. | 250/306 |
| 7,570,796 B2 | 8/2009 | Zafar et al. | |
| 7,676,077 B2 | 3/2010 | Kulkarni et al. | |
| 8,126,255 B2 | 2/2012 | Bhaskar et al. | |
| 8,664,594 B1 | 3/2014 | Jiang et al. | |
| 8,692,204 B2 | 4/2014 | Kojima et al. | |
| 8,698,093 B1 | 4/2014 | Gubbens et al. | |
| 8,716,662 B1 | 5/2014 | MacDonald et al. | |
| 2002/0148961 A1 * | 10/2002 | Nakasuji et al. | 250/311 |

(Continued)

OTHER PUBLICATIONS

International Search Report and Written Opinion for PCT/US2014/053460 mailed Dec. 16, 2014.

*Primary Examiner* — Michael P Stafira
(74) *Attorney, Agent, or Firm* — Ann Marie Mewherter (57) ABSTRACT

Systems and methods for determining one or more parameters of a wafer inspection process are provided. One method includes aligning optical image(s) of an alignment target to their corresponding electron beam images generated by an electron beam defect review system. The method also includes determining different local coordinate transformations for different subsets of alignment targets based on results of the aligning. In addition, the method includes determining positions of defects in wafer inspection system coordinates based on coordinates of the defects determined by the electron beam defect review system and the different local coordinate transformations corresponding to different groups of the defects into which the defects have been separated. The method further includes determining one or more parameters for an inspection process for the wafer based on defect images acquired at the determined positions by a wafer inspection system.

39 Claims, 4 Drawing Sheets

(56) References Cited

U.S. PATENT DOCUMENTS

| | | | |
|---|---|---|---|
| 2003/0058436 A1* | 3/2003 | Ono et al. | 356/237.2 |
| 2005/0109938 A1* | 5/2005 | Miyai et al. | 250/311 |
| 2009/0228217 A1 | 9/2009 | Fukushima | |
| 2011/0276935 A1 | 11/2011 | Fouquet et al. | |
| 2011/0299069 A1* | 12/2011 | Jang et al. | 356/237.2 |
| 2012/0004879 A1 | 1/2012 | Fukuda et al. | |
| 2012/0257041 A1 | 10/2012 | Nakagaki et al. | |
| 2013/0112893 A1 | 5/2013 | Miyake et al. | |

* cited by examiner

TUNING WAFER INSPECTION RECIPES USING PRECISE DEFECT LOCATIONS

BACKGROUND OF THE INVENTION

1. Field of the Invention

The present invention generally relates to systems and methods for tuning wafer inspection recipes using precise defect locations.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

Many different types of inspection systems have adjustable output acquisition (e.g., data, signal, and/or image acquisition) and sensitivity (or defect detection) parameters such that different parameters can be used to detect different defects or avoid sources of unwanted (nuisance) events. Although an inspection system that has adjustable output acquisition and sensitivity parameters presents significant advantages to a semiconductor device manufacturer, these inspection systems are essentially useless if the incorrect output acquisition and sensitivity parameters are used for an inspection process. In addition, since the defects, process conditions, and noise on wafers may vary dramatically (and since the characteristics of the wafers themselves may vary dramatically), the best output acquisition and sensitivity parameters for detecting the defects on a particular wafer may be difficult, if not impossible, to predict. Therefore, although using the correct output acquisition and sensitivity parameters will have a dramatic effect on the results of inspection, it is conceivable that many inspection processes are currently being performed with incorrect or non-optimized output acquisition and sensitivity parameters.

Current methods for tuning an optical inspection recipe include: (1) running a "hot" scan (i.e., one with a relatively high sensitivity (low detection threshold)), reviewing a sample (subset) of defects from the results of the inspection using a scanning electron microscope (SEM) review tool and using these defect locations to tune the recipe; or (2) obtaining images of defects from some other source such as a SEM and manually locating the defects on the wafer using various techniques and then tuning the recipe to detect those defects.

There are, however, some disadvantages of the currently used methods described above. For example, method (1) is a hit-or-miss approach based on the sample selected for SEM review. Several iterations are often needed to find suitable defects for recipe tuning since a vast majority of the "defects" detected by the sensitive recipe are nuisances (false alarms). In addition, method (2) is manual and substantially slow since it involves a human operator looking at each defect manually, and often involves destructive methods such as using "SEM burn" marks around the defect to locate it on the optical inspector.

Accordingly, it would be advantageous to develop systems and methods for determining one or more parameters of a wafer inspection process that do not have one or more of the disadvantages described above.

SUMMARY OF THE INVENTION

The following description of various embodiments is not to be construed in any way as limiting the subject matter of the appended claims.

One embodiment relates to a method for determining one or more parameters of a wafer inspection process. The method includes acquiring one or more optical images of an alignment target on a wafer generated by a wafer inspection process. The method also includes separating defects detected on the wafer into different groups. The different groups are located proximate to different subsets of alignment targets on the wafer. In addition, the method includes aligning the one or more optical images of the alignment target to their corresponding electron beam images generated by an electron beam defect review system. The method further includes determining different local coordinate transformations for the different subsets of the alignment targets based on results of the aligning step. The local coordinate transformations define relationships between coordinates determined by the electron beam defect review system and coordinates determined by the wafer inspection system. The method also includes determining positions of the defects on the wafer in wafer inspection system coordinates based on coordinates of the defects determined by the electron beam defect review system and the different local coordinate transformations for the different groups into which the defects have been separated. In addition, the method includes determining one or more parameters for an inspection process for the wafer based on defect images acquired at the determined positions by the wafer inspection system. Acquiring the one or more optical images, separating the defects, aligning the one or more optical images, determining the different local coordinate transformations, determining the positions of the defects, and determining the one or more parameters are performed with one or more computer systems.

Each of the steps of the method may be further performed as described herein. In addition, the method may include any other step(s) of any other method(s) described herein. Furthermore, the method may be performed by any of the systems described herein.

Another embodiment relates to a non-transitory computer-readable medium storing program instructions executable on a computer system for performing a computer-implemented method for determining one or more parameters of a wafer inspection process. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to determine one or more parameters of a wafer inspection process. The system includes an optical wafer inspection system configured to acquire one or more optical images of an alignment target on a wafer and defect images for the wafer. The system also includes an electron beam defect review system configured to acquire electron beam images of the alignment target. The system further includes one or more computer subsystems configured for performing the separating the defects, aligning the one or more optical images, determining the different local coordinate transformations, determining the positions of the defects, and determining the one or more parameters steps of the method described above. The system may be further configured as described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a method for determining one or more parameters of a wafer inspection process. Steps of the method described further herein such as acquiring one or more optical images, separating defects, aligning one or more optical images, determining different local coordinate transformations, determining positions of the defects, and determining one or more parameters are performed with one or more computer systems, which may be configured as described further herein. As will be described further herein, the embodiments described herein provide methods for automatically and substantially precisely locating defect locations on an optical image of a wafer, which may be stored in a system, using die layout (design) information and scanning electron microscope (SEM) image patches of the defects using a method of substantially precise alignment.

The method includes acquiring one or more optical images of an alignment target on a wafer generated by a wafer inspection system. The one or more image patches of the alignment targets along with their die locations may be added to an inspection results file described herein. However, if the locations of defects were known from some source other than an optical wafer inspection system, such as a SEM review tool, the alignment patches and locations may be added to that file. The composite file, including the defect locations and the acquired or extracted alignment patches, may then be sent to the SEM review tool along with the wafer.

Figure 1:
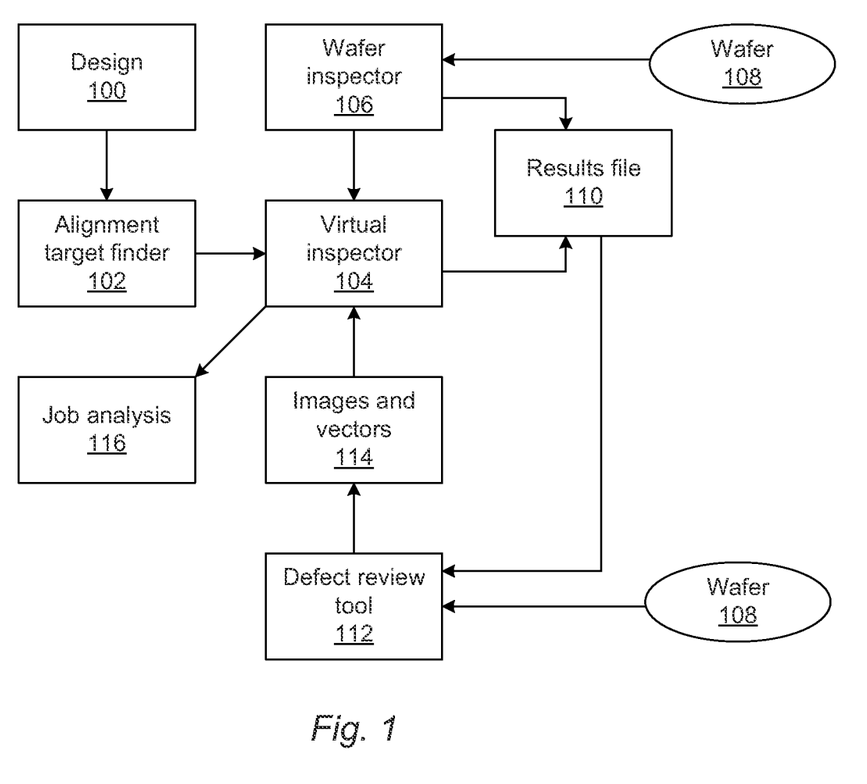
FIGS. 1-3 are flow charts illustrating embodiments of a method for determining one or more parameters of a wafer inspection process.

In one embodiment, the method includes selecting the alignment target from design layout data for the wafer. For example, as shown in FIG. 1, design 100 may be input to alignment target finder 102, which may include any suitable pattern analysis software that can be used to find alignment targets such as those described further herein in design data.

The terms "design" and "design data" as used herein generally refer to the physical design (layout) of an IC and data derived from the physical design through complex simulation or simple geometric and Boolean operations. The design may be stored in a data structure such as a GDS file, any other standard machine-readable file, any other suitable file known in the art, and a design database. A GDSII file is one of a class of files used for the representation of design layout data. Other examples of such files include GL1 and OASIS files. The design used in the embodiments described herein may be stored in any of this entire class of files irrespective of data structure configuration, storage format, or storage mechanism.

An image of a reticle acquired by a reticle inspection system and/or derivatives thereof can also be used as a "proxy" or "proxies" for the design. Such a reticle image or a derivative thereof can serve as a substitute for the design layout in any embodiments described herein that use a design. The design may include any other design data or design data proxies described in commonly owned U.S. Pat. No. 7,570,796 issued on Aug. 4, 2009 to Zafar et al, and U.S. Pat. No. 7,676,077 issued on Mar. 9, 2010 to Kulkarni et al., both of which are incorporated by reference as if fully set forth herein. In addition, the design data can be standard cell library data, integrated layout data, design data for one or more layers, derivatives of the design data, and full or partial chip design data.

In general, however, the design information or data cannot be generated by imaging a wafer with a wafer inspection system. For example, the design patterns formed on the wafer may not accurately represent the design for the wafer and the wafer inspection system may not be capable of generating images of the design patterns formed on the wafer with sufficient resolution such that the images could be used to determine information about the design for the wafer. Therefore, in general, the design information or design data cannot be generated using a physical wafer. In addition, the "design" and "design data" described herein refers to information and data that is generated by a semiconductor device designer in a design process and is therefore available for use in the embodiments described herein well in advance of printing of the design on any physical wafers.

In some embodiments, the alignment target includes one or more boundaries of repeating memory blocks. For example, the design layout of the die may be examined and software algorithms may be used to analyze the layout and automatically determine boundaries (regions) on the die containing SRAM or other repeating memory blocks. In one such example, the alignment targets may be selected by finding suitable reference locations in a design around SRAM corners. In another embodiment, the alignment target includes one or more features in a design layout for the wafer having one or more unique characteristics. For example, the algorithms described above may extract unique alignment targets scattered throughout the die (in the random logic areas) that will be used subsequently for accurate alignment.

In one embodiment, acquiring the one or more optical images of the alignment target includes acquiring the one or more optical images from a storage medium in which all image data generated for the wafer by the wafer inspection system during a scan has been stored. For example, all of the image data generated for the wafer by the wafer inspection system may be stored in a storage medium of a virtual inspection system, which may be configured as described herein, and after the alignment targets have been selected, the locations on the alignment targets in the design data may be used to determine positions of the alignment targets in the image data previously generated for the wafer. Those positions in the image data may then be used to extract image data for the alignment targets. In addition, if more than one set of image data has been generated for the wafer (e.g., using more than one optical mode of the inspection system or more than one scan of the wafer) and stored in a storage medium, the one or more optical images that are acquired for the alignment target may include one or more images for more than one of the alignment targets. In this manner, more than one image may be acquired for any one alignment target.

In another embodiment, the one or more computer systems include a virtual wafer inspection system configured to acquire the one or more optical images of the alignment target by extracting the one or more optical images from image data generated for the wafer by the wafer inspection system during a scan. For example, the virtual wafer inspection system may automatically extract optical image patches at the boundaries of the memory blocks and the other unique alignment points described above. The virtual wafer inspection system may be configured as described in U.S. Pat. No. 8,126,255 issued on Feb. 18, 2012 to Bhaskar et al., which is incorporated by reference as if fully set forth herein. The virtual wafer inspection systems described in this patent may be configured to perform any step(s) of any methods described herein. The virtual wafer inspection system may be configured to extract the one or more optical images of the alignment target as described further above.

As shown in FIG. 1, in some such embodiments, alignment target finder 102 may output results including any information about the selected alignment targets to virtual inspector 104. Virtual inspector 104 may be configured to store image data generated by wafer inspector 106 for wafer 108 during an inspection process. Wafer inspector 106 may have generated results file 110 for wafer 108 that includes information about defects detected on the wafer during the inspection process and any other suitable information about the wafer generated during or as a result of the inspection process. Virtual inspector 104 may extract optical images for the alignment targets selected by alignment target finder 102 from the image data received from wafer inspector 106. The virtual inspector may also add the extracted optical images for the alignment targets and information about their locations on the wafer to results file 110.

The method also includes separating defects detected on the wafer into different groups. The different groups are located proximate to different subsets of alignment targets on the wafer. In this manner, the defects may be separated into groups based on their proximity to one or more of the alignment target patches.

In one embodiment, the defects that are separated into the different groups are detected on the wafer by the wafer inspection system. For example, a wafer may be scanned by an optical inspector and the optical image(s) of the wafer may be stored on a system such as a virtual wafer inspection system. Defect locations on the wafer may also be recorded in an inspection results file such as a lot results file or other suitable file formats. The defect locations and the images of the wafer may be stored in the same or different files.

In another embodiment, the defects that are separated into the different groups are detected on the wafer by one or more other wafer inspection systems. For example, the defects may be detected on one wafer inspection system, and then the positions of the defects in wafer inspection system coordinates for another wafer inspection system may be determined as described herein. In this manner, defects detected with one wafer inspection system may be located with substantially high precision on another wafer inspection system or in image data generated by the other wafer inspection system. The other wafer inspection system(s) may include any suitable commercially available wafer inspection system(s).

In some embodiments, the one or more computer systems include a computer subsystem of the electron beam defect review system configured to perform at least the separating step. For example, a SEM review tool may group the defects by their proximity to one or more of the alignment target patches, which may be provided by a virtual wafer inspection system. The computer subsystem of the electron beam defect review system may be further configured as described herein.

The method further includes aligning the one or more optical images of the alignment target to their corresponding electron beam images generated by an electron beam defect review system. For example, for each defect group, the method may include using the SEM review tool to first move to the corresponding alignment location, acquire an image of an appropriate size (field of view), align the optical patch image with the SEM image using known image processing techniques, and note the alignment offset between the SEM patch and the optical patch. This may be repeated for (say) 3 such alignment patches close to this group of defects. As shown in FIG. 1, in some embodiments, results file 110, which may include wafer inspection results for wafer 108 and images for the alignment targets, which may have been extracted by the virtual inspector, may be provided to defect review tool 112. Wafer 108 may also be transferred to the defect review tool. The defect review tool may then acquire electron beam images for the alignment targets by imaging wafer 108 based on information about the alignment targets contained in results file 110. The electron beam images for the alignment targets may then be aligned to the optical images as described above.

The method also includes determining different local coordinate transformations for the different subsets of the alignment targets based on results of the aligning step. The local coordinate transformations define relationships between coordinates determined by the electron beam defect review system and coordinates determined by the wafer inspection system. For example, knowing the locations of the 3 alignment targets and the corresponding 3 SEM targets, the local coordinate transformation (to map optical to SEM coordinate space) to obtain the substantially precise defect locations in the group can be determined. The acquired SEM patches, the coordinates on the SEM, along with the coordinate transformations (mapping optical coordinates to SEM coordinates)

applied to locate defects in each group on the SEM can be sent back to the virtual wafer inspection system. For example, as shown in FIG. 1, defect review tool 112 may generate images and vectors 114 (where "vectors" refers to the transformations described herein), which may include electron beam images of the alignment targets and at least some of the defects detected on the wafer, and a file containing information about images and vectors 114 may be sent back to virtual inspector 104.

The method further includes determining positions of the defects on the wafer in wafer inspection system coordinates based on coordinates of the defects determined by the electron beam defect review system and the different local coordinate transformations for the different groups into which the defects have been separated. In some embodiments, the positions of the defects in the wafer inspection system coordinates are determined on an optical pixel grid. For example, the virtual wafer inspection system can apply the inverse of the coordinate transforms to map the substantially precise defect locations back to the optical pixel grid. For defects that were detected by the optical inspector on the image stored in the virtual inspection system, this transformation is unnecessary since the defect location is known on the optical pixel grid. However, for defects that were not detected by the optical inspector but whose SEM image was obtained on this review tool (for example, by manually or automatically examining a region around certain "known" locations obtained from external sources), this inverse transformation is required to map its location onto the optical pixel grid.

In one embodiment in which the defects that are separated into the different groups are detected on the wafer by the wafer inspection system, the method includes acquiring electron beam images of the defects with the electron beam defect review system. For example, the defect review tool may perform local de-skew of defects near reference locations, perform "short distance" moves to corrected locations of defects, and grab SEM defect patches.

In another embodiment in which the defects that are separated into the different groups are detected on the wafer by the wafer inspection system, the method includes acquiring electron beam images of the defects with the electron beam defect review system by moving from the alignment target in one of the different subsets to only the defects in one of the different groups corresponding to the one of the different subsets. For example, for defect locations obtained from an optical inspector image (whose reference patches were provided as a reference), the SEM review tool can make a relatively short distance move from one of the reference locations to each of the defects in the group (in some optimal manner to minimize positioning errors) and acquire SEM images of the defects.

In some embodiments in which the defects that are separated into the different groups are not detected on the wafer by the wafer inspection system, the method includes acquiring electron beam images of the defects by searching for the defects on the wafer with the electron beam defect review system. For example, for defects obtained from some external source, whose locations are only approximately known (e.g., with respect to the die origin or center of the wafer), the review tool can be used either manually or automatically to hunt around those locations and record image patches where defects were found and their locations in SEM coordinate space.

In one embodiment, the one or more computer systems includes a virtual wafer inspection system configured to perform at least the determining the positions of the defects step. For example, once the local coordinate transformations are determined, the transformations can be used by the virtual inspection system to determine the positions of the defects. The virtual inspection system can then acquire optical images of the defects at the determined positions. For example, the virtual inspection system can extract optical images of the defects at the determined positions from previously stored image data for the wafer. In addition, or alternatively, the virtual inspection system can instruct or control the optical wafer inspection system to acquire optical images at the determined positions. In this manner, the virtual wafer inspection system can acquire defect images on tool. In some instances, the virtual wafer inspection system may extract images at the determined positions of the defects, determine if the images that are available are sufficient for determining parameter(s) of an inspection process as described further herein, and if the images are not sufficient, then determine one or more parameters of the inspection system with which images at the determined positions should be acquired. The images with the new wafer inspection system parameters may be acquired by the optical wafer inspection system or by the virtual inspection system via optical wafer inspection system control.

The method also includes determining one or more parameters for an inspection process for the wafer based on detect images acquired at the determined positions by the wafer inspection system. The one or more parameters may be determined for an existing inspection process, in which case, determining the one or more parameters may involve tuning or updating the inspection process. The one or more parameters determined for the inspection process can be stored in any suitable inspection process recipe (where a "recipe" can be generally defined as a set of instructions that a tool can use to perform a process). Since the embodiments described herein can determine the positions of the defects substantially accurately in wafer inspection system coordinates, the embodiments described herein can be used for tuning wafer inspection recipes using substantially precise defect locations. Although the embodiments are described herein as obtaining substantially precise defect location information from an electron beam defect review tool, the embodiments described herein can be used to tune an inspection recipe for a patterned wafer on an optical inspector using substantially precise defect location information obtained from some other source such as a SEM, electrical testing results, test structures on a semiconductor wafer, or some other form of imaging source. The embodiments described herein can, however, also be used to determine one or more parameters for a new, not previously existing, inspection process recipe. In addition, the embodiments described herein can perform any other suitable functions using substantially precise defect locations from other tools using predetermined reference alignment points extracted from design.

The embodiments described herein can also be performed using any defects (e.g., defects found in the discovery phase or research and development) for tuning recipes for production. For example, defect of interest (DOI) discovery at a semiconductor manufacturing fab happens on a highly sensitive inspection tool or combination of inspection tools. For production, only a single tool is used to monitor defect activities. Assessing the capability of a specific tool to monitor key DOIs currently involves substantially tedious manual effort. However, the embodiments described herein can be used to assess the sensitivity automatically for a specific tool on a virtual wafer inspection system or an optical wafer inspection system based on a list of DOI locations. The embodiments described herein can be used to produce a recipe with the best detection sensitivity.

In some instances, as shown in FIG. 1, virtual inspector 104 may be used to determine the one or more parameters of the inspection process, which may include job (image frame) analysis 116. For example, the virtual inspection system may analyze frames (jobs) containing defect locations and provide signal-to-noise measurements and/or graphical output. However, virtual inspector 104 may also be configured to perform any other suitable functions using image data stored therein for a wafer based on the determined positions for the defects. In this manner, output of the virtual inspection system may include results of a number of different functions performed by virtual inspector 104 on image data for wafer 108 and based on images and vectors 114 provided by defect review tool 112.

In one embodiment in which the defects that are separated into the different groups are not detected on the wafer by the wafer inspection system, the method includes acquiring electron beam images of the defects on the wafer with the electron beam defect review system and acquiring the defect images with the wafer inspection system based on the positions of the defects in the wafer inspection system coordinates. In this manner, in some embodiments, the defect images are acquired after the positions of the defects on the wafer in the wafer inspection system coordinates have been determined. For example, it can be difficult to locate defects in an optical wafer image given an image of the defect acquired from another source such as a SEM review tool. However, using the coordinate transformations determined as described herein, information about a defect detected by a SEM review tool can be used with a coordinate transformation described herein to locate the defect in images of the wafer produced by an optical wafer inspection system. In this manner, when defects are discovered on a SEM review tool, the defects can be located with the wafer inspection system with substantially high precision using the positions of the defects determined as described herein. In this manner, any uncertainty that the correct defect is being imaged by the wafer inspection system can be substantially eliminated.

In another embodiment, the defect images are acquired before the positions of the defects on the wafer in the wafer inspection system coordinates have been determined. For example, if image data for a wafer is stored in the virtual inspection system prior to the method being performed, then acquiring the defect images may include extracting image data at the determined positions from stored image data for a wafer. In one such example, the virtual wafer inspection system described herein can locate defects in wafer images using reference-to-optical reference alignment and displacement vectors.

In some embodiments, the one or more parameters include one or more parameters of a defect detection algorithm applied to output generated for the wafer during the inspection process. For example, once the defect locations are known on the optical pixel grid, the defect detection algorithm can be tuned using image frames from those die areas (or using additional die regions) to tune the inspection recipe. In one such example, given SEM images of defects in SRAM, the embodiments described herein can drive back to a stored wafer image and analyze the signal-to-noise. The one or more parameters of the defect detection algorithm that are determined by the embodiments described herein may include any parameters of any defect detection algorithm.

In an additional embodiment, the one or more parameters include one or more parameters of an optical subsystem of the wafer inspection system with which output is generated for the wafer during the inspection process. The one or more parameters of the optical subsystem may include any parameters of an optical subsystem of a wafer inspection system such as illumination wavelength(s), illumination polarization(s), angle(s) of incidence, angle(s) of collection, collection wavelength(s), collection polarization(s), etc. The parameter(s) of the optical subsystem may be determined based on the defect images in any suitable manner.

Figure 2:
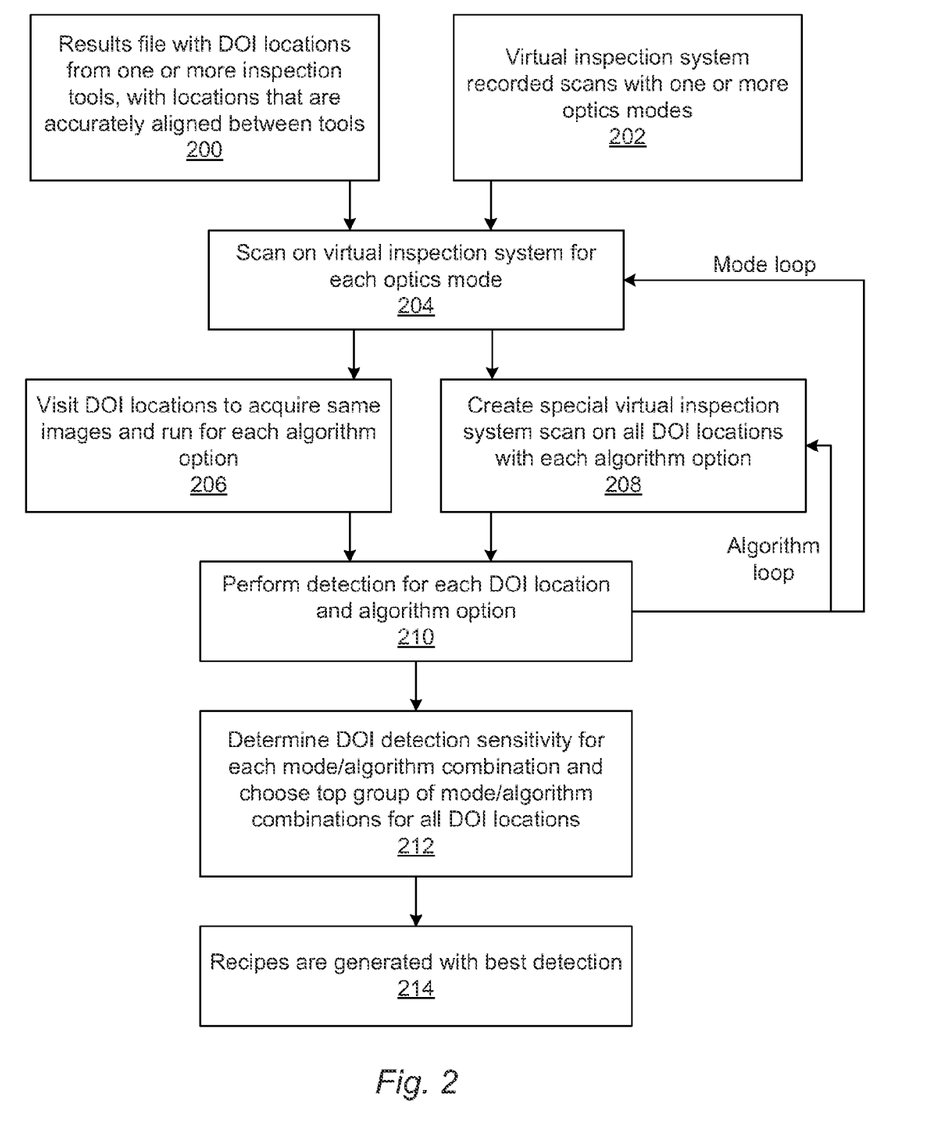

Determining one or more parameters of a defect detection algorithm may also include automatic sensitivity assessment and algorithm recipe generation based on a list of DOI locations. FIG. 2 illustrates one embodiment of sensitivity assessment and automatic algorithm recipe generation performed on a virtual wafer inspection system. For example, as shown in FIG. 2, a virtual inspection system may use results file 200 with DOI locations from one or more inspection tools, with locations that are accurately aligned between tools, and virtual inspection system recorded scans 202 with one or more optical modes to perform step 204 that includes scanning on the virtual wafer inspection system for each optics mode. The one or more inspection tools from which the DOI locations are acquired may include a baseline tool or a combination of multiple baseline tools. The DOI locations may be aligned substantially accurately between the baseline tool(s) and the current tool (i.e., the inspection system for which the one or more parameters are being determined) as described herein. The virtual inspection system recorded scans with one or more optics modes may be acquired using the current tool with a basic recipe defined.

The method shown in FIG. 2 may also include step 206 or step 208. In step 206, DOI locations may be visited to acquire the same images and run for each algorithm option. In step 208, a special virtual inspection system scan may be created on all DOI locations with each algorithm option. The method also includes step 210 in which detection for each DOI location and algorithm option is performed. In some instances, if the results of step 210 are unsatisfactory, then the method may repeat steps 204, 206 (or 208), and 210 in a mode loop in which the optics modes are changed until step 210 produces satisfactory results. In addition, if the results of step 210 are unsatisfactory, then the method may repeat steps 206 (or 208) and 210 in an algorithm loop in which parameters of the algorithm(s) are changed until step 210 produces satisfactory results. The method may then include step 212 in which the virtual inspection system is used to determine DOI detection sensitivity for each mode/algorithm combination and to choose the top group of mode/algorithm combinations for all DOI locations. In addition, the method includes step 214 in which the recipe(s) are generated with the best detection.

Figure 3:
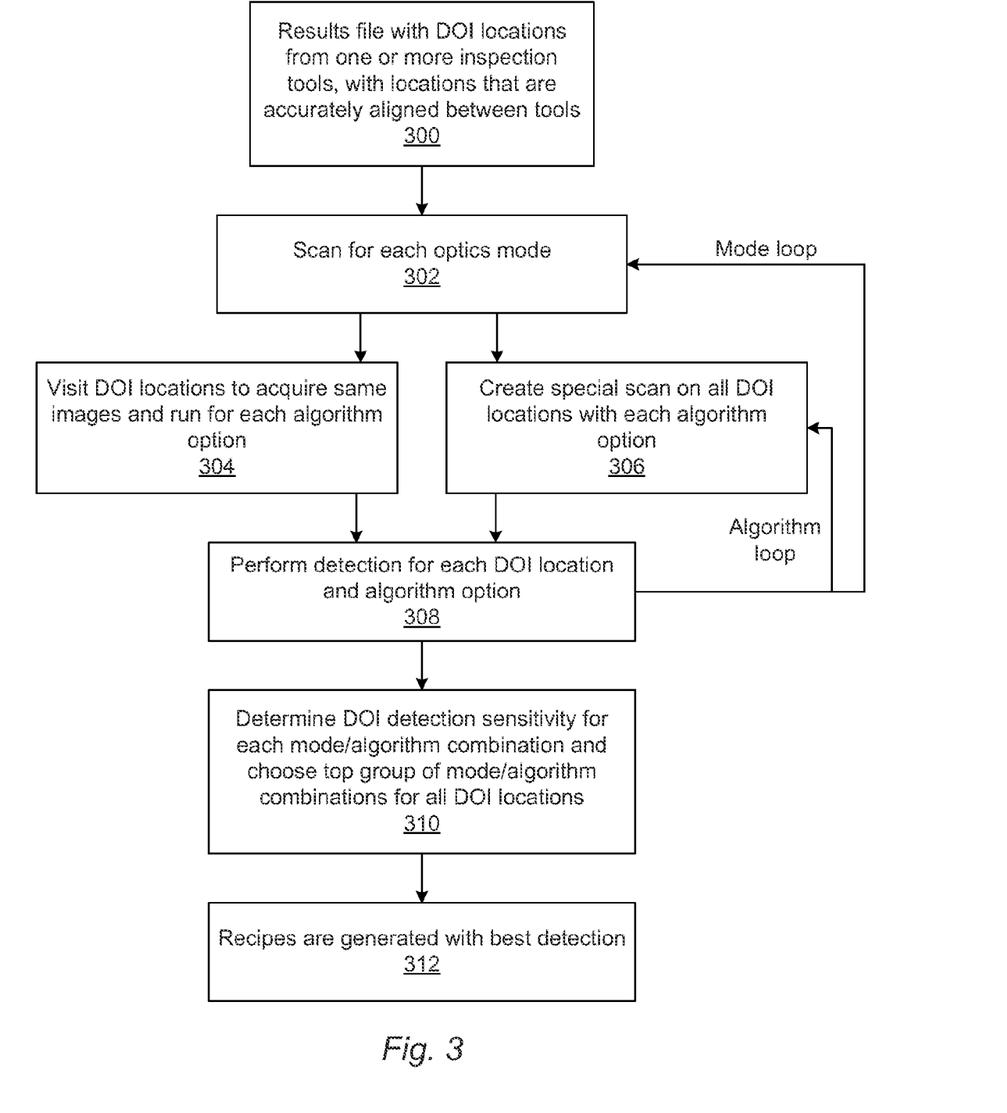

FIG. 3 illustrates one embodiment of sensitivity assessment and automatic algorithm recipe generation performed on an optical wafer inspection system. For example, as shown in FIG. 3, an actual wafer inspection system may use results file 300 with DOI locations from one or more inspection tools, with locations that are accurately aligned between tools to perform step 302 that includes scanning on the actual wafer inspection system for each optics mode. The one or more inspection tools from which the DOI locations are acquired may include a baseline tool or a combination of multiple baseline tools. The locations may be aligned substantially accurately between the baseline tool(s) and the current tool (i.e., the inspection system for which the one or more parameters are being determined) as described herein.

The method shown in FIG. 3 may also include step 304 or step 306. In step 304, DOI locations may be visited to acquire the same images and run for each algorithm option. In step 306, a special inspection system scan may be created on all DOI locations with each algorithm option. The method also includes step 308 in which detection for each DOI location and algorithm option is performed. In some instances, if the results of step 308 are unsatisfactory, then the method may repeat steps 302, 304 (or 306) and 308 in a mode loop in which the optics modes are changed until step 308 produces satisfactory results. In addition, if the results of step 308 are unsatisfactory, then the method may repeat steps 304 (or 306) and 308 in an algorithm loop in which parameters of the algorithm(s) are changed until step 308 produces satisfactory results. The method may then include step 310 in which the inspection system is used to determine DOI detection sensitivity for each mode/algorithm combination and to choose the top group of mode/algorithm combinations for all DOI locations. In addition, the method includes step 312 in which the recipe(s) are generated with the best detection.

Each of the embodiments of the methods described above may include any other step(s) of any other method(s) described herein. Furthermore, each of the embodiments of the methods described above may be performed by any of the systems described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Figures 4, 5:
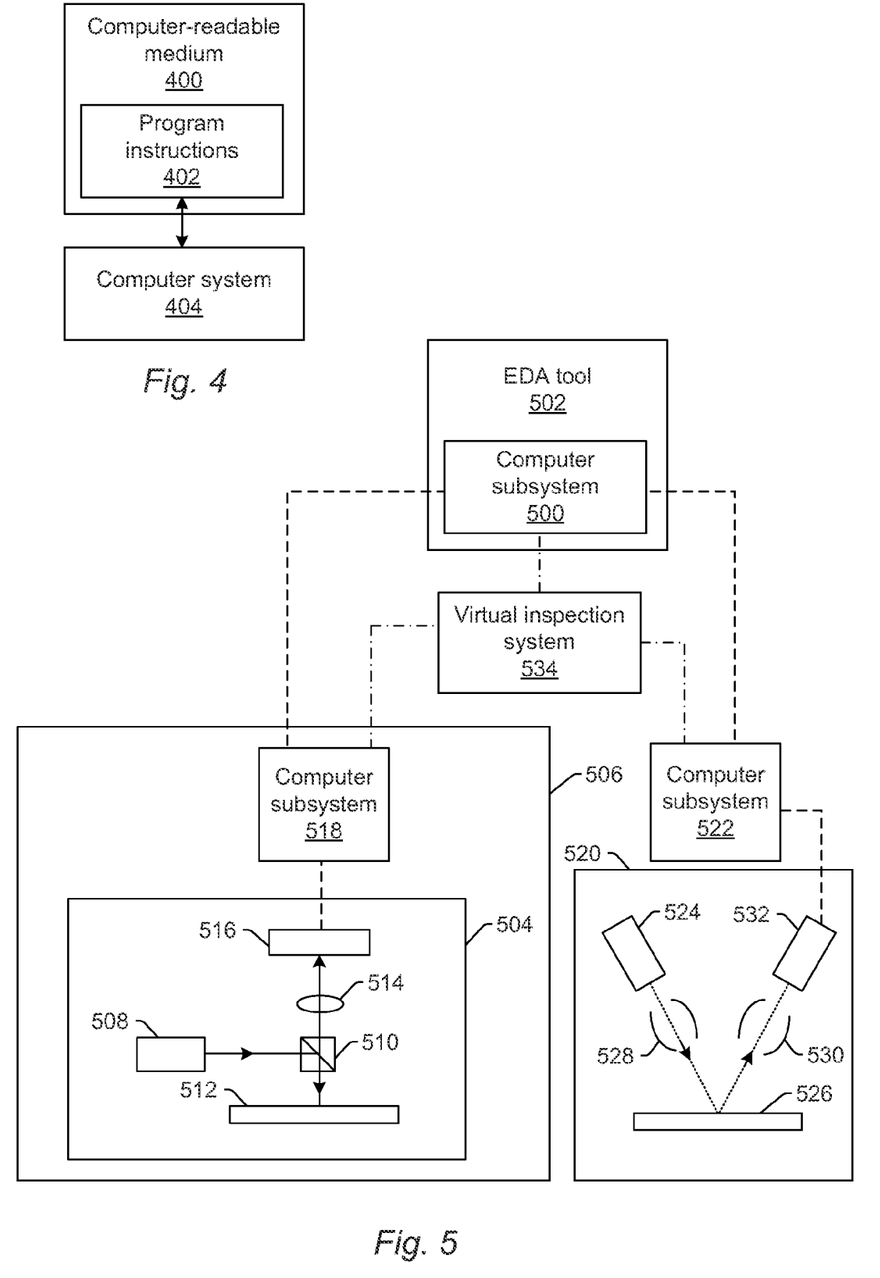
FIG. 4 is a block diagram illustrating one embodiment of a non-transitory computer-readable medium storing program instructions for causing a computer system to perform a computer-implemented method described herein.
FIG. 5 is a schematic diagram illustrating a side view of an embodiment of a system configured to determine one or more parameters of a wafer inspection process.

Another embodiment relates to a non-transitory computer-readable medium storing program instructions executable on a computer system for performing computer-implemented method for determining one or more parameters of a wafer inspection process. One such embodiment is shown in FIG. 4. For example, as shown in FIG. 4, non-transitory computer-readable medium 400 stores program instructions 402 executable on computer system 404 for performing a computer-implemented method for determining one or more parameters of a wafer inspection process. The computer-implemented method may include any step(s) of any method(s) described herein.

Program instructions 402 implementing methods such as those described herein may be stored on non-transitory computer-readable medium 400. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 404 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

An additional embodiment relates to a system configured to determine one or more parameters of a wafer inspection process. The system includes one or more computer subsystems configured for performing the steps of separating defects, aligning optical image(s), determining different local coordinate transformations, determining positions of the defects, and determining one or more parameters described further herein. The computer subsystem(s) may be configured to perform these step as described further herein.

In one embodiment, the computer subsystem(s) described above include one or more computer subsystems that are part of an electronic design automation (EDA) tool, and the optical wafer inspection system and electron beam defect review system described further herein are not part of the EDA tool. For example, as shown in FIG. 5, the computer subsystem(s) described above may include computer subsystem 500 included EDA tool 502. The EDA tool and the computer subsystem(s) included in such a tool may include any commercially available EDA tool that can be configured to perform one or more of the steps described above. For instance, the computer subsystem(s) that are configured to select the alignment target(s) from design layout data for a wafer may include such computer subsystem(s). In this manner, the design layout data may be processed by one system or tool to select the alignment target(s) that will be used by another, different system or tool to determine substantially precise defect positions in wafer inspection system coordinates.

The computer subsystem(s) that are used to select the alignment target(s) also may not be part of an EDA tool and may be included in another system or tool or simply be configured as a stand alone computer system. Furthermore, the tool or computer subsystem that selects the alignment target(s) may be configured to provide that information to the other tool by storing or transferring information for the alignment target(s) to a shared computer-readable storage medium such as a fab database or by transmitting information for the alignment target(s) directly to the tool that will use it, which may be performed as described further herein.

The system also includes an optical wafer inspection system configured to acquire optical image(s) of alignment target(s) on a wafer and defect images for the wafer. One embodiment of such an optical wafer inspection system is shown in FIG. 5 as system 506 that includes optical subsystem 504. The optical wafer inspection system is configured for scanning the wafer with light and detecting light from the wafer during the scanning. For example, as shown in FIG. 5, the optical subsystem includes light source 508, which may include any suitable light source known in the art.

Light from the light source may be directed to beam splitter 510, which may be configured to direct the light from the light source to wafer 512. The light source may be coupled to any other suitable elements (not shown) such as one or more condensing lenses, collimating lenses, relay lenses, objective lenses, apertures, spectral filters, polarizing components and the like. As shown in FIG. 5, the light may be directed to the wafer at a normal angle of incidence. However, the light may be directed to the wafer at any suitable angle of incidence including near normal and oblique incidence. In addition, the light or multiple light beams may be directed to the wafer at more than one angle of incidence sequentially or simultaneously. The inspection system may be configured to scan the light over the wafer in any suitable manner.

Light from wafer 512 may be collected and detected by one or more detectors of the optical subsystem during scanning. For example, light reflected from wafer 512 at angles relatively close to normal (i.e., specularly reflected light when the incidence is normal) may pass through beam splitter 510 to lens 514. Lens 514 may include a refractive optical element as shown in FIG. 5. In addition, lens 514 may include one or more refractive optical elements and/or one or more reflective optical elements. Light collected by lens 514 may be focused to detector 516. Detector 516 may include any suitable detector known in the art such as a charge coupled device (CCD) or another type of imaging detector. Detector 516 is configured to generate output that is responsive to the reflected light collected by lens 514. Therefore, lens 514 and detector 516 form one channel of the optical subsystem. This channel of the optical subsystem may include any other suitable optical components (not shown) known in the art. The output of the detector may include, for example, images, image data, signals, image signals, or any other output that can be generated by a detector suitable for use in an inspection system.

Since the inspection system shown in FIG. 5 is configured to detect light specularly reflected from the wafer, the inspection system is configured as a bright field (BF) inspection system. Such an inspection system may, however, also be configured for other types of wafer inspection. For example, the inspection system shown in FIG. 5 may also include one or more other channels (not shown). The other channel(s) may include any of the optical components described herein such as a lens and a detector, configured as a scattered light channel. The lens and the detector may be further configured as described herein. In this manner, the inspection system may also be configured for dark field (DF) inspection.

The computer subsystem(s) of the inspection system may use output generated by detector 516 and/or any other detectors included in the inspection system to detect defects on the wafer as described herein. For example, the system may also include computer subsystem 518 that is coupled to the optical subsystem. In this manner, output generated by the detector(s) of the optical subsystem may be provided to computer subsystem 518. Computer subsystem 518 may be configured to perform any other steps described herein.

Computer subsystem 518 may also be coupled to the other computer subsystem that is not part of the inspection system such as computer subsystem 500, which may be included in another tool such as the EDA tool described above such that computer subsystem 518 can receive output generated by computer subsystem 500, which may include, for example, the information for the alignment target(s). For example, the two computer subsystems may be effectively coupled by a shared computer-readable storage medium such as a fab database or may be coupled by a transmission medium such as that described above such that information may be transmitted between the two computer subsystems.

The system shown in FIG. 5 also includes an electron beam defect review system configured to acquire electron beam images of the alignment target(s). The electron beam defect review system shown in FIG. 5 includes electron column 520 coupled to computer subsystem 522. The electron column includes electron beam source 524 configured to generate electrons that are focused to wafer 526 by one or more elements 528. The electron beam source may include, for example, a cathode source or emitter tip, and one or more elements 528 may include, for example, a gun lens, an anode, a beam limiting aperture, a gate valve, a beam current selection aperture, an objective lens, and a scanning subsystem, all of which may include any such suitable elements known in the art. Electrons returned from the wafer (e.g., secondary electrons) may be focused by one or more elements 530 to detector 532. One or more elements 530 may include, for example, a scanning subsystem, which may be the same scanning subsystem included in element(s) 528. The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein. Although the electron column is shown in FIG. 5 as being configured such that the electrons are directed to the wafer at an oblique angle of incidence and are scattered from the wafer at another oblique angle, it is to be understood that the electron beam may be directed to and scattered from the wafer at any suitable angles.

Computer subsystem 522 may be coupled to detector 532 as described above. The detector may detect electrons returned from the surface of the wafer thereby forming images of the wafer. The images may include any of the electron beam images described herein. Computer subsystem 522 may be configured to perform any step(s) described herein. Computer subsystem 522 may also be coupled to another computer subsystem such as computer subsystem 500 of the EDA tool in the same manner as described above.

The system shown in FIG. 5 may also include virtual inspection system 534. The virtual inspection system may be configured as described further herein. In addition, in the embodiment shown in FIG. 5, the virtual inspection system may be coupled to the computer subsystem of the EDA tool (e.g., so that the virtual inspection system can receive information about the design and/or alignment target(s) from the EDA tool), the computer subsystem of the optical wafer inspection system (e.g., so that the virtual inspection system can receive image data, inspection results, and any other information generated by the inspection system), and the computer subsystem of the electron beam defect review system (e.g., such that the virtual inspection system can receive electron beam images, coordinate transformations, etc. from the electron beam defect review system). The virtual inspection system may be coupled to such computer subsystems as described above. In addition, the virtual inspection system may be coupled to the computer subsystems such that the virtual inspection system can send information to the other computer subsystems. The virtual inspection system may be configured to perform any step(s) of any embodiment(s) described herein.

It is noted that FIG. 5 is provided herein to generally illustrate a configuration of an inspection system and defect review system that may be included in the system embodiments described herein. Obviously, the inspection and defect review system configurations described herein may be altered to optimize the performance of the inspection system and defect review system as is normally performed when designing commercial inspection and defect review systems. In addition, the systems described herein may be implemented using an existing inspection system and/or existing defect review system (e.g., by adding functionality described herein to an existing inspection or defect review system) such as the 29xx/28xx series of tools that are commercially available from KLA-Tencor, Milpitas, Calif. For some such systems, the methods described herein may be provided as optional functionality of the system in addition to other functionality of the system). Alternatively, the system described herein may be designed "from scratch" to provide a completely new system.

Further modifications and alternative embodiments of various aspects of the invention will be apparent to those skilled in the art in view of this description. For example, systems and methods for tuning wafer inspection recipes using precise defect locations are provided. Accordingly, this description is to be construed as illustrative only and for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for determining one or more parameters of a wafer inspection process, comprising:
   acquiring one or more optical images of an alignment target on a wafer generated by a wafer inspection system;
   separating defects detected on the wafer into different groups, wherein the different groups are located proximate to different subsets of alignment targets on the wafer;
   aligning the one or more optical images of the alignment target to their corresponding electron beam images generated by an electron beam defect review system;
   determining different local coordinate transformations for the different subsets of the alignment targets based on results of the aligning step, wherein the local coordinate transformations define relationships between coordinates determined by the electron beam defect review system and coordinates determined by the wafer inspection system;
   determining positions of the defects on the wafer in wafer inspection system coordinates based on coordinates of the defects determined by the electron beam defect review system and the different local coordinate transformations for the different groups into which the defects have been separated; and
   determining one or more parameters for an inspection process for the wafer based on defect images acquired at the determined positions by the wafer inspection system, wherein acquiring the one or more optical images, separating the defects, aligning the one or more optical images, determining the different local coordinate transformations, determining the positions of the defects, and determining the one or more parameters are performed with one or more computer systems.

2. The method of claim 1, wherein the defects that are separated into the different groups are detected on the wafer by the wafer inspection system.

3. The method of claim 1, wherein the defects that are separated into the different groups are detected on the wafer by one or more other wafer inspection systems.

4. The method of claim 1, further comprising selecting the alignment target from design layout data for the wafer.

5. The method of claim 1, wherein the alignment target comprises one or more boundaries of repeating memory blocks.

6. The method of claim 1, wherein the alignment target comprises one or more features in a design layout for the wafer having one or more unique characteristics.

7. The method of claim 1, wherein acquiring the one or more optical images of the alignment target comprises acquiring the one or more optical images from a storage medium in which all image data generated for the wafer by the wafer inspection system during a scan has been stored.

8. The method of claim 1, wherein the one or more computer systems comprise a virtual wafer inspection system configured to acquire the one or more optical images of the alignment target by extracting the one or more optical images from image data generated for the wafer by the wafer inspection system during a scan.

9. The method of claim 1, wherein the one or more computer systems comprise a computer subsystem of the electron beam defect review system configured to perform at least the separating the defects step.

10. The method of claim 1, wherein the defects that are separated into the different groups are detected on the wafer by the wafer inspection system, and wherein the method further comprises acquiring electron beam images of the defects with the electron beam defect review system.

11. The method of claim 1, wherein the defects that are separated into the different groups are detected on the wafer by the wafer inspection system, and wherein the method further comprises acquiring electron beam images of the defects with the electron beam defect review system by moving from the alignment target in one of the different subsets to only the defects in one of the different groups corresponding to the one of the different subsets.

12. The method of claim 1, wherein the defects that are separated into the different groups are not detected on the wafer by the wafer inspection system, and wherein the method further comprises acquiring electron beam images of the defects by searching for the defects on the wafer with the electron beam defect review system.

13. The method of claim 1, wherein the one or more computer systems comprise a virtual wafer inspection system configured to perform at least the determining the positions of the defects step.

14. The method of claim 1, wherein the positions of the defects in the wafer inspection system coordinates are determined on an optical pixel grid.

15. The method of claim 1, wherein the defects that are separated into the different groups are not detected on the wafer by the wafer inspection system, and wherein the method further comprises acquiring electron beam images of the defects on the wafer with the electron beam defect review system and acquiring the defect images with the wafer inspection system based on the positions of the defects in the wafer inspection system coordinates.

16. The method of claim 1, wherein the defect images are acquired after the positions of the defects on the wafer in the wafer inspection system coordinates have been determined.

17. The method of claim 1, wherein the defect images are acquired before the positions of the defects on the wafer in the wafer inspection system coordinates have been determined.

18. The method of claim 1, wherein the one or more parameters comprise one or more parameters of a defect detection algorithm applied to output generated for the wafer during the inspection process.

19. The method of claim 1, wherein the one or more parameters comprise one or more parameters of an optical subsystem of the wafer inspection system with which output is generated for the wafer during the inspection process.

20. A non-transitory computer-readable medium, storing program instructions executable on a computer system for performing a computer-implemented method for determining one or more parameters of a wafer inspection process, wherein the computer-implemented method comprises:
   acquiring one or more optical images of an alignment target on a wafer generated by a wafer inspection system;
   separating defects detected on the wafer into different groups, wherein the different groups are located proximate to different subsets of alignment targets on the wafer;

aligning the one or more optical images of the alignment target to their corresponding electron beam images generated by an electron beam defect review system;

determining different local coordinate transformations for the different subsets of the alignment targets based on results of the aligning step, wherein the local coordinate transformations define relationships between coordinates determined by the electron beam defect review system and coordinates determined by the wafer inspection system;

determining positions of the defects on the wafer in wafer inspection system coordinates based on coordinates of the defects determined by the electron beam defect review system and the different local coordinate transformations for the different groups into which the defects have been separated; and determining one or more parameters for an inspection process for the wafer based on defect images acquired at the determined positions by the wafer inspection system.

21. A system configured to determine one or more parameters of a wafer inspection process, comprising:

an optical wafer inspection system configured to acquire one or more optical images of an alignment target on a wafer and defect images for the wafer;

an electron beam defect review system configured to acquire electron beam images of the alignment target; and one or more computer subsystems configured for:

separating defects detected on the wafer into different groups, wherein the different groups are located proximate to different subsets of alignment targets on the wafer;

aligning the one or more optical images of the alignment target to their corresponding electron beam images;

determining different local coordinate transformations for the different subsets of the alignment targets based on results of the aligning step, wherein the local coordinate transformations define relationships between coordinates determined by the electron beam defect review system and coordinates determined by the optical wafer inspection system;

determining positions of the defects on the wafer in wafer inspection system coordinates based on coordinates of the defects determined by the electron beam defect review system and the different local coordinate transformations for the different groups into which the defects have been separated; and determining one or more parameters for an inspection process for the wafer based on the defect images acquired at the determined positions by the wafer inspection system.

22. The system of claim 21, wherein the defects that are separated into the different groups are detected on the wafer by the optical wafer inspection system.

23. The system of claim 21, wherein the defects that are separated into the different groups are detected on the wafer by one or more other wafer inspection systems.

24. The system of claim 21, wherein the one or more computer subsystems are further configured for selecting the alignment target from design layout data for the wafer.

25. The system of claim 21, wherein the alignment target comprises one or more boundaries of repeating memory blocks.

26. The system of claim 21, wherein the alignment target comprises one or more features in a design layout for the wafer having one or more unique characteristics.

27. The system of claim 21, wherein the one or more computer subsystems are further configured for acquiring the one or more optical images from a storage medium in which all image data generated for the wafer by the optical wafer inspection system during a scan has been stored.

28. The system of claim 21, wherein the one or more computer subsystems comprise a virtual wafer inspection system configured to acquire the one or more optical images of the alignment target by extracting the one or more optical images from image data generated for the wafer by the optical wafer inspection system during a scan.

29. The system of claim 21, wherein the one or more computer subsystems comprise a computer subsystem of the electron beam defect review system.

30. The system of claim 21, wherein the defects that are separated into the different groups are detected on the wafer by the optical wafer inspection system, and wherein the electron beam defect review system is further configured to acquire electron beam images of the defects.

31. The system of claim 21; wherein the defects that are separated into the different groups are detected on the wafer by the optical wafer inspection system, and wherein the electron beam defect review system is further configured to acquire electron beam images of the defects by moving from the alignment target in one of the different subsets to only the defects in one of the different groups corresponding to the one of the different subsets.

32. The system of claim 21, wherein the defects that are separated into the different groups are not detected on the wafer by the optical wafer inspection system, and wherein the electron beam defect review system is further configured to acquire electron beam images of the defects by searching for the defects on the wafer.

33. The system of claim 21, wherein the one or more computer subsystems comprise a virtual wafer inspection system.

34. The system of claim 21, wherein the positions of the defects in the wafer inspection system coordinates are determined on an optical pixel grid.

35. The system of claim 21, wherein the defects that are separated into the different groups are not detected on the wafer by the optical wafer inspection system, wherein the electron beam defect review system is further configured to acquire electron beam images of the defects, and wherein the optical wafer inspection system is further configured to acquire the defect images with the optical wafer inspection system based on the positions of the defects in the wafer inspection system coordinates.

36. The system of claim 21, wherein the defect images are acquired after the positions of the defects on the wafer in the wafer inspection system coordinates have been determined.

37. The system of claim 21, wherein the defect images are acquired before the positions of the defects on the wafer in the wafer inspection system coordinates have been determined.

38. The system of claim 21, wherein the one or more parameters comprise one or more parameters of a defect detection algorithm applied to output generated for the wafer during the inspection process.

39. The system of claim 21, wherein the one or more parameters comprise one or more parameters with which output is generated for the wafer during the inspection process.

* * * * *